United States Patent [19]
Calello et al.

[11] Patent Number: 6,143,283
[45] Date of Patent: *Nov. 7, 2000

[54] GLOSSY TRANSFER RESISTANT LIPSTICK COMPOSITIONS

[75] Inventors: Joseph Frank Calello, Union; Anjali Abhimanyu Patil, Westfield, both of N.J.; Salvatore Joseph Barone, Staten Island, N.Y.; Ann Marshall Krog, Red Bank, N.J.

[73] Assignee: Revlon Consumer Products Corporation, New York, N.Y.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 09/141,313

[22] Filed: Aug. 27, 1998

Related U.S. Application Data

[63] Continuation of application No. 08/670,827, Jun. 20, 1996, Pat. No. 5,849,275.
[60] Provisional application No. 60/000,505, Jun. 26, 1995.

[51] Int. Cl.[7] .................................................. A61K 7/027
[52] U.S. Cl. ............................. 424/64; 424/63; 424/401; 424/DIG. 5; 424/78.17; 424/78.03; 514/63
[58] Field of Search ............................... 424/63, 64, 401, 424/DIG. 5, 78.17, 78.03; 514/63

[56] References Cited

U.S. PATENT DOCUMENTS

| | | | |
|---|---|---|---|
| 4,693,935 | 9/1987 | Mazurek | 428/352 |
| 4,981,902 | 1/1991 | Mitra | 524/547 |
| 4,981,903 | 1/1991 | Garbe | 524/547 |
| 5,061,481 | 10/1991 | Suzuki | 424/63 |
| 5,219,560 | 6/1993 | Suzuki | 424/63 |
| 5,468,477 | 11/1995 | Kumar | 424/78.17 |
| 5,470,551 | 11/1995 | Dubief | 424/70.12 |
| 5,505,937 | 4/1996 | Castrogiovanni | 424/64 |
| 5,567,428 | 10/1996 | Hughes | 424/401 |
| 5,800,316 | 9/1998 | Brieva et al. | 424/63 |

FOREIGN PATENT DOCUMENTS 2785692  12/1996  France .

OTHER PUBLICATIONS

3M Brand Silicones "Plus" Polymers (1994).

*Primary Examiner*—Raj Bawa
*Attorney, Agent, or Firm*—Julie Blackburn

[57] ABSTRACT

A cosmetic composition having improved transfer resistance comprising:

a) from about 0.1–60% of a copolymer which is an adhesive at room temperature, b) from about 0.1–60% by weight of a volatile solvent having a viscosity of 0.5 to 20 centipoise at 25° C., c) 0.1–60% by weight of a nonvolatile oil.

d) 0.1–80% dry particulate matter.

6 Claims, No Drawings

GLOSSY TRANSFER RESISTANT LIPSTICK COMPOSITIONS

This is a continuation of application Ser. No. 08/670,827, filed Jun. 20, 1996, now U.S. Pat. No. 5,849,275, which claims priority from Provisional patent application Ser. No. 60/000,505 filed Jun. 26, 1995.

TECHNICAL FIELD

The invention is in the field of cosmetic compositions applied to the skin or hair.

BACKGROUND OF THE INVENTION

Cosmetic compositions are generally defined as compositions suitable for application to the human body. Cosmetic compositions such as creams and lotions are used to moisturize the skin and keep it in a smooth supple condition. Pigmented cosmetic compositions such as makeup, blush, lipstick, and eyeshadow, are used to color the skin and lips. Since color is one of the most important reasons for wearing cosmetics, color containing cosmetics must be very carefully formulated to provide maximum wear and effect:

One of the long standing problems with makeups such as face makeup, lipstick, mascara, and the like, is the tendency of the cosmetic to blot or transfer from the skin or lashes onto other surfaces such as glassware, silverware, or clothing. This not only creates soiling, but forces the cosmetic user to reapply cosmetic at fairly short intervals.

Cosmetic compositions with improved transfer resistance are disclosed in U.S. Pat. No. 5,505,937. However, these transfer resistant cosmetic compositions have a very matte texture on the skin and lips.

Marketing studies indicate that approximately three out of every five women prefer lipsticks which are glossy because they provide a dewy look which is associated with youthfulness and good health. However, the traditional lipstick formulas provide very matte finishes, as do the transfer resistant lipsticks which are currently so popular. If ingredients which provide enhanced gloss are added to transfer resistant cosmetics in attempt to improve gloss, the transfer resistance tends to be compromised. Accordingly, there is a great desire to achieve cosmetic compositions with excellent adhesion to the skin, or superior transfer resistance, and at the same time provide high gloss.

The object of this invention is to formulate a cosmetic compositions, particularly a lipstick, with long lasting adherence to skin and which also has gloss and shine.

Another object of the invention is to formulate a high gloss high shine cosmetic which yields a film which does not readily transfer to clothing or utensils.

Another object of the invention is to formulate a cosmetic which yields a film which exhibits reduced permeability to oil and water.

Unless otherwise indicated, all percentages and ratios expressed herein are by weight.

SUMMARY OF THE INVENTION

The invention is directed to a cosmetic composition with gloss and shine having improved transfer resistance:

a) from about 0.1–60% by weight of a polymer which is an adhesive at room temperature, b) from about 0.1–70% by weight of a volatile solvent having a viscosity of 0.5 to 20 centipoise at 25° C., c) 0.1–60% of a nonvolatile oil d) 0.1–80% dry particulate matter.

DETAILED DESCRIPTION

The composition of the invention contains 0.1–60%, preferably 0.5–50%, more preferably 1–30% of a polymer which is an adhesive at room temperature. The phrase "adhesive at room temperature" means that at approximately 20° C. the polymer exhibits good affinity to skin. Such polymers may be liquids or solids, and if solids, generally have a melting point of up to 200° C. They are soluble or dispersible in nonpolar solvents. The polymer is of a density, molecular weight, and melting point such that when it is mixed with the volatile solvent in the disclosed proportions it is capable of forming a solid or gel.

In one preferred embodiment of the invention comprises a vinyl, methacrylic, or acrylic backbone and has pendant siloxane groups and pendant fluorochemical groups. Such polymers preferably comprise comprise repeating A, C, D and optionally B monomers wherein:

A is at least one free radically polymerizable acrylic or methacrylic ester of a 1,1,-dihydroperfluoroalkanol or analog thereof, omega-hydridofluoroalkanols, fluoroalkylsulfonamido alcohols, cyclic fluoroalkyl alcohols, and fluoroether alcohols, B is at least one reinforcing monomer copolymerizable with A, C is a monomer having the general formula $X(Y)_n Si (R)_{3-m} Z_m$ wherein X is a vinyl group copolymerizable with the A and B monomers, Y is a divalent linking group which is alkylene, arylene, alkarylene, and aralkylene of 1 to 30 carbon atoms which may incorporate ester, amide, urethane, or urea groups, n is zero or 1;

m is an integer of from 1 to 3,

R is hydrogen, $C_{1-4}$ alkyl, aryl, or alkoxy,

Z is a monovalent siloxane polymeric moiety; and

D is at least one free radically polymerizable acrylate or methacrylate copolymer, Such polymers and their manufacture are disclosed in U.S. Pat. Nos. 5,209,924 and 4,972,037, which are hereby incorporated by reference.

Preferred is wherein the polymer is a combination of A, C, and D monomers wherein A is a polymerizable acrylic or methacrylic ester of a fluoroalkylsulfonamido alcohol, and where D is a methacrylic acid ester of a $C_{1-2}$ straight or branched chain alcohol, and C is as defined above. Most preferred is a polymer having moieties of the general formula:

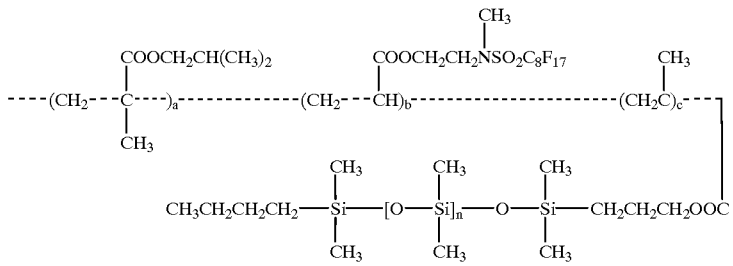

wherein a, b, and c are 1–100,000, and the terminal groups can be $C_{1-20}$ straight or branched chain alkyl, aryl, alkoxy, and the like. These polymers may be purchased from Minnesota Mining and Manufacturing Company under the tradenames "Silicone Plus" polymers. Most preferred is poly (isobutyl methacrylate -co- methyl FOSEA) -g- poly (dimethylsiloxane) which is sold under the tradename SA 70-5 IBMMF.

In another preferred embodiment of the invention, the polymer has a vinyl, methacrylic, or acrylic polymeric backbone with pendant siloxane groups. Such polymers as disclosed in U.S. Pat. Nos. 4,693,935, 4,981,903, 4,981,902, and which are hereby incorporated by reference. Preferably, these polymers are comprised of A, C, and optionally B monomers wherein:

A is at least on free radically polymerizable vinyl, methacrylate, or acrylate monomer;

B, when present, is at least one reinforcing monomer copolymerizable with A,

C is a monomer having the general formula:

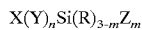

wherein:

X is a vinyl group copolymerizable with the A and B monomers;

Y is a divalent linking group;

n is zero or 1;

m is an integer of from 1 to 3;

R is hydrogen, $C_{1-10}$ alkyl, substituted or unsubstituted phenyl, $C_{1-10}$ alkoxy;

Z is a monovalent siloxane polymeric moiety.

Examples of A monomers are lower to intermediate methacrylic acid esters of $C_{1-12}$ straight or branched chain alcohols, styrene, vinyl esters, vinyl chloride, vinylidene chloride, acryloyl monomers, and so on.

The B monomer, if present, is a polar acrylic or methacrylic monomer having at least one hydroxyl, amino, or ionic group (such as quaternary ammonium, carboxylate salt, sulfonic acid salt, and so on).

The C monomer is as above defined.

In a third preferred embodiment of the invention, the preferred polymer is vinyl-silicone graft or block copolymer having the formula:

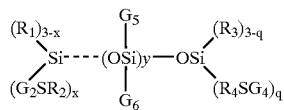

wherein $G_5$ represents monovalent moieties which can independently be the same or different selected from the group consisting of alky, aryl, aralkyl, alkoxy, alkylamino, fluoroalkyl, hydrogen, and -ZSA; A represents a vinyl polymeric segment consisting essentially of a polymerized free radically polymerizable monomer, and Z is a divalent linking group such as $C_{1-10}$ alkylene, aralkylene, arylene, and alkoxylalkylene, most preferably Z methylene or propylene.

$G_6$ is a monovalent moiety which can independently be the same or different selected from the group consisting of alkyl, aryl, aralkyl, alkoxy, alkylamino, fluoroalkyl, hydrogen, and -ZSA;

$G_2$ comprises A;

$G_4$ comprises A;

$R_1$ is a monovalent moiety which can independently be the same or different and is selected from the group consisting of alkyl, aryl, aralkyl, alkoxy, alkylamino, fluoroalkyl, hydrogen, and hydroxyl; but preferably $C_{1-4}$ alkyl or hydroxyl, and most preferably methyl.

$R_2$ is independently the same or different and is a divalent linking group such as $C_{1-10}$ alkylene, arylene, aralkylene, and alkoxyalkylene, preferably $C_{1-3}$ alkylene or $C_{7-10}$ aralkylene, and most preferably —$CH_2$— or 1,3-propylene, and $R_3$ is a monovalent moiety which is independently alkyl, aryl, aralkyl, alkoxy, alkylamino, fluoroalkyl, hydrogen, or hydroxyl, preferably $C_{1-4}$ alkyl or hydroxyl, most preferably methyl;

$R_4$ is independently the same or different and is a divalent linking group such as $C_{1-10}$ alkylene, arylene, aralkylene, alkoxyalkylene, but preferably $C_{1-3}$ alkylene and $C_{7-10}$ alkarylene, most preferably —$CH_2$— or 1,3-propylene.

x is an integer of 0–3;

y is an integer of 5 or greater; preferably 10 to 270, and more preferably 40–270;

q is an integer of 0–3.

These polymers are described in U.S. Pat. No. 5,468,477, which is hereby incorporated by reference. Most preferred is poly(dimethylsiloxane)-g-poly(isobutyl methacrylate), which is manufactured by 3-M Company under the tradename VS 70 IBM.

THE VOLATILE SOLVENT

The volatile solvents of the invention generally have a low viscosity ranging from 0.1 to 20, and more preferably 0.5–10 centipoise at 25° C. The term "volatile" means that the solvent has a measureable vapor pressure, or in other words a vapor pressure of at least 2 mm. of mercury at 20° C. Volatile solvents suitable in the composition of the invention include volatile low viscosity silicone fluids such as cyclic silicones having the formula:

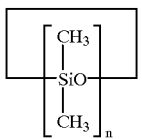

wherein n=3-7. Volatile linear polydimethylsiloxanes are also suitable and generally have from about 2 to 9 silicon atoms and are of the formula:

wherein n=0-7. These silicones are available from various sources including Dow Corning Corporation and General Electric. Dow Corning silicones are sold under the tradenames Dow Corning 244, 245, 344, 345, and 200 fluids. These fluids comprise octamethylcyclotetrasiloxane, decamethylcyclopentasiloxane, hexamethyldisiloxane, or mixtures thereof.

Also suitable as the volatile solvent component are straight or branched chain paraffinic hydrocarbons having 5–20 carbon atoms, more preferably 10–16 carbon atoms. Suitable hydrocarbons are pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70 to 190, more preferably 160–180, and a boiling point range of 30 to 320° C., preferably 60–260° C., a viscosity of less than 20 centipoise at 25° C. Such paraffinic hydrocarbons are available from EXXON under the ISOPARS trademark, and Permethyl Corporation. Such $C_{5-20}$ paraffinic hydrocarbons such as $C_{12}$ isoparaffin manufactured by the Permethyl Corporation having the tradename Permethyl 99 A™, or a $C_{12}$ isoparaffin (isododecane) are distributed by Presperse having the tradename Permetlyl 99A™. Various $C_{16}$ isoparaffins commercially available, such as isohexadecane (having the tradename Permethyl R™) are also suitable. The volatile solvent may be a mixture of volatile silicone and paraffinic hydrocarbons; a ratio of 1:20 to 20:1 respectively is suggested. The volatile solvent preferably ranges from 1–60%, or 10–60% by weight of the total composition.

THE NONVOLATILE OIL

The nonvolatile oil ranges from 0.1–40%, preferably 0.5–30% by weight of the composition. The term "nonvolatile" means that the oil does not have a measureable vapor pressure, or in other words a vapor pressure of less than 2 mm. of mercury at 20° C. Preferably, the nonvolatile oil has a viscosity ranging from 10 to 1,000,000 centipoise at 25° C., preferably 20 to 600,000 centipoise at 25° C.

The nonvolatile oil may comprise esters of the formula RCO-OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the C.T.F.A. Cosmetic Ingredient Handbook, First Edition, 1988, which is hereby incorporated by reference.

The nonvolatile oil may also comprise glyceryl esters of fatty acids, or triglycerides, such as castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the nonvolatile oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the nonvolatile oil are nonvolatile hydrocarbons such as isoparaffins, hydrogenated polyisobutene, mineral oil, squalene, petrolatum, and so on.

Also suitable as the nonvolatile oil are various lanolin derivatives such as acetylated lanolin, acetylated lanolin alcohol, and so on.

Nonvolatile nonfluorinated silicones are also suitable as the nonvolatile component. Such silicones preferably have a viscosity of 10 to 600,000 centistokes, preferably 20 to 100,000 centistokes at 25° C. Suitable silicones include amodimethicone, bisphenylhexamethicone, dimethicone, dimethicone copolyol, dimethiconol, hexadecyl methicone, hexamethyldisiloxane, methicone, phenyl trimethicone, simethicone, dimethylhydrogensiloxane, stearoxy dimethicone, stearoxytrimethylsilane, vinyldimethicone, and mixtures thereof. Such silicones are available from Dow Corning as the 3225C formulation aid, Dow 190 and 193 fluids, or similar products marketed by Goldschmidt under the ABIL tradename.

Also suitable as the nonvolatile oil are various fluorinated oils such as fluorinated silicones or perfluropolyethers. Particularly suitable are fluorosilicones such as trimethylsilyl endcapped fluorosilicone oil, polytrifluoropropylrnethylsiloxanes, and similar silicones such as those disclosed in U.S. Pat. No. 5,118,496 which is hereby incorporated by reference. The nonvolatile component may comprise mixtures of fluorosilicones and dimethylpolysiloxanes. The nonvolatile component may also comprise perfluoropolyethers like those disclosed in U.S. Pat. Nos. 5,183,589, 4,803,067, 5,183,588 all of which are hereby incorporated by reference. These perfluoropolyethers are commercially available from Montefluos under the trademark Fomblin.

Other suitable nonvolatiles include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

THE DRY PARTICULATE MATTER

Preferably, the compositions of the invention contain 0.1–80%, preferably 0.1–60%, more preferably 0.1–50% dry particulate matter having a particle size of 0.02 to 200, preferably 0.5 to 100 microns. The particulate matter may be colored or non-colored (for example white). Suitable such powders include bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The powder component may also comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarine and chromium or chromium hydroxide colors, and mixtures thereof. Other pigments such as manganese violet, carmine, iron blue (or ferric ammonium ferrocyanide) are also suitable.

Obviously the percentage of pigments used in the powder component will depend upon the type of cosmetic being formulated. Blushes, eyeshadows, lipsticks and similar cosmetics will contain higher percentages of pigment in the powder phase, usually ranging from 5–50% of the total cosmetic composition. Preferably a combination of pigments and non-pigment powders are present, and the pigment:non-pigment powder weight ratio ranges from 1:20 to 20:1.

The cosmetic compositions of the invention may be in the form of anhydrous compositions or water and oil emulsions.

Preferably the cosmetic compositions are anhydrous cosmetic sticks such as lipstick, eyeshadow sticks, concealer sticks, blush sticks, and the like. Preferred cosmetic stick compositions comprise:

0.1–30% polymer,
10–60% volatile solvent,
0.1–30% nonvolatile oil,
5–50% dry particulate matter, and
1–50% wax.

Suitable wax or wax-like materials generally have a melting point range of 25 to 140° C. Waxes in this category include synthetic waxes such as polyethylenes and derivatives thereof, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof.

Preferably the cosmetic compositions are anhydrous lipsticks composition comprises:

0.1–30% of a polymer selected from the group consisting of poly(dimethylsiloxane)-g-poly(isobutyl methacrylate), poly(isobutyl methacrylate-co-methyl FOSEA)-g-poly(dimethylsiloxane), and mixtures thereof;
10–60% of a volatile solvent which is a volatile silicone, volatile paraffinic hydrocarbon, or mixtures thereof,
0.1–30% of a nonvolatile oil,
5–50% of a dry particulate matter having a particle size of 0.02 to 100 microns, and
1–50% of a wax having a melting point of 25–140° C.

In addition, cosmetic stick compositions may additionally contain one or more of preservatives, antioxidants, emulsifiers, thickeners, and so on. The ingredients corresponding to these categories are set forth in the *C.T.F.A. Cosmetic Ingredient Handbook,* First Edition, 1988, which is hereby incorporated by reference.

Creams or lotions are generally water-in-oil or oil-in-water emulsions containing water, humectants, surfactants, preservatives, sunscreens, dry particulate matter, and the like. Generally the ranges of these ingredients are 0.1–80% water, 0.01–10% humectants, 0.01–5% surfactants, 0.001–5% preservatives, and 0.001–5% sunscreens. Suitable emollients, humectants, surfactants, preservatives and sunscreens are as set forth in the *C.T.F.A. Cosmetic Ingredient Handbook,* First Edition, 1988, which is hereby incorporated by reference.

Creams may be anhydrous, or aqueous, and contain water, humectants, surfactants, thickeners, sunscreens, preservatives, and sunscreens, as mentioned above, may also be included.

The creams and lotions of the invention are particularly good vehicles for sunscreen. In particular, about 0.01–10% by weight of various sunscreen compounds such as PABA, cinnamates, benzophenones, and derivatives thereof can be incorporated into the cream or lotion. Because the compositions exhibit superior transfer resistance characteristics, the sunscreens are able to remain on the skin for a longer time period. Suitable creams in accordance with the invention are sunscreen creams comprising:

1–30% polymer
1–40% volatile solvent
0.5–30% nonvolatile oil
0.1–70% dry particulate matter.

The dry particulate matter is largely titanium dioxide and other powdered materials which provide good sunscreen protection.

The compositions of the invention may also be in the form of face powders comprising:

0.1–60% polymer,
0.1–60% of a volatile solvent having a viscosity of 0.5 to 20 centipoise at 25° C.,
0.1–60% of a nonvolatile oil, and
0.01–80% of a dry particulate matter.

The composition of the invention may also be incorporated into mascaras which generally comprise film formers, waxes, emulsifiers, and pigment.

Suitable mascara compositions comprise:

0.1–15% polymer
0.1–40 of a volatile solvent having a viscosity of 0.5 to 20 centipoise at 25° C.,
0.1–10% of a nonvolatile oil,
0.1–30% of a dry particulate matter,
0.1–20% film former,
0.1–30% wax, and
0.1–10% emulsifier.

Preferably, the volatile solvent comprises a mixture of volatile silicone and a volatile hydrocarbon, and the dry particulate matter comprises a combination of pigments and non-pigment powders.

Suitable waxes are as set forth above. Suitable film formers include acacia gum, cellulose derivatives, guar derivatives and all those set forth on pages 68–69 of the *C.T.F.A. Cosmetic Ingredient Handbook,* First Edition, 1988, which is hereby incorporated by reference.

Suitable emulsifiers or emulsifying agents are as set forth on pages 90 to 94 of the *C.T.F.A. Cosmetic Ingredient Handbook,* First Edition, 1988, which is hereby incorporated by reference.

The composition of the invention may also be incorporated into water and oil emulsion makeup compositions. Makeup generally contains water, and pigment in addition to an oil phase. Suitable cosmetic makeup compositions comprise:

0.1–20% polymer 0.1–40% of a volatile solvent having a viscosity of 0.5 to 20 centipoise at 25° C., 0.1–25% of a nonvolatile oil, 0.1–70% dry particulate matter having a particle size of 0.02 to 100 microns, and 0.1–50% water.

Preferably, the nonvolatile oils are dimethicone and dimethicone copolyol, and the pigment to non-pigment powder weight ratio is 1:20 to 20:1.

The cosmetically acceptable vehicle may also be a blush. Preferred are blush compositions comprising:

0.1–20% polymer, 0.1–30% of a volatile solvent having a viscosity of 0.5 to 20 centipoise at 25° C., 0.1–25% of a nonvolatile oil, 0.1–10% water, and 0.1–70% dry particulate matter having a particle size of 0.02 to 100 microns.

In the above composition, it is preferred that the nonvolatile oils are dimethylhydrogen siloxane, dimethicone, dimethiconol, and fluorosilicone.

The cosmetically acceptable vehicle may also be an eyeshadow. Eyeshadows generally contain pigment or powder in addition to waxes and oils. Preferred eyeshadow compositions comprise:

0.1–20% polymer, 0.1–30% of a volatile solvent having a viscosity of 0.5 to 20 centipoise at 25° C., 0.1–40% nonvolatile oil, 0.1–60% dry particulate matter having a particle size of 0.02 to 100 microns.

In the above eyeshadow composition, it is preferred that the volatile solvent comprises cyclomethicone and the nonvolatile oil comprises dimethiconol.

The cosmetically acceptable vehicle may also be a concealer, which generally comprises pigment or other powder, wax, and other ingredients such as humectants, preservatives, etc. A preferred composition of the invention is a concealer comprising:

0.1–15% polymer, 0.1–40% of a volatile solvent having a viscosity of 0.5 to 20 centipoise at 25° C., 0.1–35% of a nonvolatile oil, and 0.1–40% of a dry particulate matter having a particle size of 0.02 to 100 microns.

In this concealer composition it is preferred that the nonvolatile oil comprises fluorinated silicone, dimethylpolysiloxane or mixtures thereof.

The compositions of the invention provide cosmetics which adhere well to the skin and exhibit reduced transfer resistance.

The invention will be further described in connection with the following examples which are set forth for the purpose of illustration only.

EXAMPLE 1

A transfer resistant lipstick composition in the stick form was made as follows:

|  | w/w % |
|---|---|
| Synthetic wax | 7.00 |
| Ceresin | 3.50 |
| Ozokerite | 2.25 |
| Paraffin | 2.00 |
| Octyldodecanol, cholesterol, trilaurin phospholipids, glycosphingolipids | 0.50 |
| Illipe butter | 0.20 |
| Polypropylene | 0.10 |
| Methyl paraben | 0.30 |
| Propyl paraben | 0.10 |
| BHA | 0.10 |
| SA-70SIBMMF (25% in cyclomethicone)* | 10.50 |
| Vitamin E acetate | 0.10 |
| Apple extract/vegetable oil | 0.50 |
| Phytantriol | 0.10 |
| Vitamin A & D3 corn oil | 0.20 |
| Maleated soybean oil | 0.50 |
| Isostearyltrimethylolpropanesiloxysilicate/black iron oxide | 0.08 |
| Mica, lecithin | 14.37 |
| Mica | 2.50 |
| Titanium dioxide, mica | 2.00 |
| Titanium dioxide, mica, iron oxide | 1.00 |
| Isododecane | 12.00 |
| Cyclomethicone | 29.60 |

*3-M, poly(isobutyl methacrylate-co-methyl FOSEA)-g-poly (dimethylsiloxane)

The ingredients were heated, mixed, and poured into sticks. The sticks were hard, and when applied provided a slightly transfer proof finish that did not kiss off when the lips were placed on the back of the hand. The stick provided a muted glossy, dewy finish on the lips.

EXAMPLE 2

|  | w/w % | | |
|---|---|---|---|
|  | eyeshadow | blush | concealer |
| Coco caprylate/caprate | 2.200 | 2.200 | 2.200 |
| Cetyl acetate/acetylated lanolin alcohol | 1.000 | 1.000 | 1.000 |
| SA-70SIBMMF (25% in cyclomethicone) | 7.000 | 7.000 | 7.000 |
| Synthetic wax | 6.600 | 6.600 | 6.600 |
| Ceresin wax | 4.000 | 4.000 | 4.000 |
| Paraffin wax | 3.000 | 3.000 | 3.000 |
| Ozokerite | 1.000 | 1.000 | 1.000 |
| Octyldodecanol/trilaurin/ phospholipid/cholesterol/ glycosphingolipid | 0.500 | 0.500 | 0.500 |
| Illipe butter | 0.200 | 0.200 | 0.200 |
| Polypropylene | 0.100 | 0.100 | 0.100 |
| Methyl paraben | 0.300 | 0.300 | 0.300 |
| Propyl paraben | 0.100 | 0.100 | 0.100 |
| BHA | 0.100 | 0.100 | 0.100 |
| Lanolin oil | 3.500 | 3.500 | 3.500 |
| D&C red 7 ca lake | — | 2.100 | — |
| FD&C yellow 5 al lake | — | 0.800 | — |
| Red iron oxide | 2.100 | — | 2.100 |
| Yellow iron oxide | 0.800 | — | 0.800 |

-continued

|  | w/w % | | |
|---|---|---|---|
|  | eyeshadow | blush | concealer |
| Black iron oxide | 0.500 | 0.500 | 0.100 |
| Titanium dioxide | 0.100 | 0.100 | 0.100 |
| Bismuth oxychloride | 3.000 | 3.000 | 3.000 |
| Titanium dioxide/mica | 9.000 | 9.000 | 9.000 |
| Cyclomethicone | 41.40 | 41.400 | 41.400 |
| Mica/dimethicone | 2.000 | 2.000 | 2.000 |
| Isododecane | 9.000 | 9.000 | 9.000 |
| Trioctyldodecyl citrate | 2.000 | 2.000 | 2.000 |
| Cococaprylate/caprate | 0.500 | 0.500 | 0.500 |

The above cosmetic compositions were made by first mixing the dry ingredients. The waxes and oils were added with heating to about 100° C. The volatile solvent and polymer were added. The remaining ingredients were added and the mixture stirred before pouring the mixtures into the appropriate molds and allowing to cool.

EXAMPLE 3

A transfer resistant lipstick composition in accordance with the invention was made as follows:

|  | w/w % |
|---|---|
| Synthetic wax | 7.00 |
| Ceresin | 3.50 |
| Ozokerite | 2.25 |
| Paraffin | 2.00 |
| Octyldodecanol, cholesterol, trilaurin phospholipids, glycosphingolipids | 0.50 |
| Illipe butter | 0.20 |
| Polypropylene | 0.10 |
| Methyl paraben | 0.30 |
| Propyl paraben | 0.10 |
| BHA | 0.10 |
| VS 70 IBM in Finsolv (25% in cyclomethicone)* | 10.50 |
| Vitamin E acetate | 0.10 |
| Apple extract/vegetable oil | 0.50 |
| Phytantriol | 0.10 |
| Vitamin A & D3 corn oil | 0.20 |
| Maleated soybean oil | 0.50 |
| Isostearyltrimethylolpropanesiloxysilicate/black iron oxide | 0.08 |
| Mica, lecithin | 14.37 |
| Mica | 2.50 |
| Titanium dioxide, mica | 2.00 |
| Titanium dioxide, mica, iron oxide | 1.00 |
| Isododecane | 12.00 |
| Cyclomethicone | 29.60 |

*3-M Company, poly(dimethylsiloxane)-g-poly(isobutyl methacrylate)

EXAMPLE 4

A glossy transfer resistant lip gel was made as follows:

|  | w/w % |
|---|---|
| VS70-5¹ in isododecane (50/50) | 13.00 |
| SA70-5² in cyclomethicone (25/75) | 53.00 |
| Dimethicone (0.65 cs) | 27.00 |
| Diisostearyl fumerate | 7.00 |

¹Poly(dimethylsiloxane)-g-poly(isobutyl methacrylate)
²Poly(isobutyl methacrylate-co-methyl FOSEA-g-polydimethylsiloxane)

The gel provides a very smooth, glossy finish when applied to the lips and does not transfer off.

EXAMPLE 5

A lip gel with gloss and transfer resistance was made as follows:

|  | w/w % |
|---|---|
| SA70-5¹ in cyclomethicone (25/75) | 51.00 |
| VS70-5² in isododecane | 14.50 |
| Dimethicone (0.65 cs) | 27.00 |
| Diisostearyl fumerate | 7.00 |
| Synthetic hydrocarbons | 0.50 |

While the invention has been described in connection with preferred embodiments, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A lipstick composition comprising, by weight of the total composition:

a) 0.5–30% of a vinyl silicone graft or block copolymer having the formula:

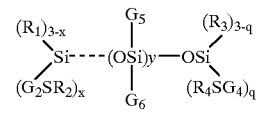

wherein $G_5$ represents monovalent moieties which can independently be the same or different selected from the group consisting of alkyl, aryl, aralkyl, alkoxy, alkylamino, fluoroalkyl, hydrogen, and —ZSA; A represents a vinyl polymeric segment consisting essentially of a polymerized free radically polymerizable monomer, and Z is a divalent linking group such as $C_{1-10}$ alkylene, aralkylene, arylene, and alkoxylalkylene, $G_6$ is a monovalent moiety which can independently be the same or different selected from the group consisting of alkyl, aryl, aralkyl alkoxy, alkylamino, fluoroalkyl, hydrogen, and —ZSA;

$G_2$ comprises A;

$G_4$ comprises A;

$R_1$ is a monovalent moiety which can independently be the same or different and is selected from the group consisting of alkyl aryl, aralkyl, alkoxy, alkylamino, fluoroalkyl, hydrogen, and hydroxyl;

$R_2$ is independently the same or different and is a divalent liking group such as $C_{1-10}$ alkylene, arylene, aralkylene, and alkoxyalkylene, and $R_3$ is a monovalent moiety which is independently alkyl, aryl, aralkyl, alkoxy, alkylamino, fluoroalkyl, hydrogen, or hydroxyl;

$R_4$ is independently the same or different and is a divalent linking group such as $C_{1-10}$ alkylene, arylene, aralkylene, alkoxyalkylene, x is an integer of 0–3;

y is an integer of 5 or greater;

q is an integer of 0–3.

b) 10–60% of cyclomethicone, c) 0.5–30% of a nonvolatile oil selected from the group consisting of
   i) esters of the formula RCO—OR' wherein R and R' are each independently a $C_{1-24}$ straight or branched chain alkyl alkenyl, or alkoxycarbonylalkyl, or alkylcarbonyloxyalkyl,
   ii) glyceryl esters,
   iii) nonvolatile hydrocarbons,
   iv) lanolin and lanolin derivatives,
   v) nonvolatile. nonfluorinated silicones,
   vi) fluorinated silicones,
   vii) perfluoropolyethers,
   viii) sorbitan derivatives,
   ix) and mixtures thereof,
d) 0.1–50% of dry particulate matter having a particle size of 0.5 to 100 microns, and
e) 1–50% of a wax having a melting point of 25 to 140° C.

2. The composition of claim 1 wherein the nonvolatile oil is dimethicone or polytrifluoropropylmethylsiloxane.

3. The composition of claim 1 wherein the dry particulate matter comprises a mixture of pigment and powder and the weight ratio is from 1:20 to 20:1 respectively.

4. The composition of claim 1 wherein the wax is selected from the group consisting of polyethylene wax and ozokerite.

5. The composition of claim 1 wherein the wax is ozokerite.

6. The composition of claim 1 wherein the nonvolatile silicone oil is dimethicone or phenyl trimethicone.

* * * * *